United States Patent [19]

Blöcker

[11] Patent Number: 5,114,839
[45] Date of Patent: May 19, 1992

[54] PROCESS FOR DNA SEQUENCING USING OLIGONUCLEOTIDE BANK

[75] Inventor: Helmut Blöcker, Braunschweig, Fed. Rep. of Germany

[73] Assignee: Gesellschaft fur biotechnologische Forsching mbH, Braunschweig, Fed. Rep. of Germany

[21] Appl. No.: 457,815

[22] PCT Filed: May 24, 1989

[86] PCT No.: PCT/EP89/00579

§ 371 Date: Jan. 11, 1990

§ 102(e) Date: Jan. 11, 1990

[87] PCT Pub. No.: WO89/11211

PCT Pub. Date: Nov. 30, 1989

[30] Foreign Application Priority Data

May 24, 1988 [DE] Fed. Rep. of Germany ....... 3817591

[51] Int. Cl.⁵ .................. C07H 1/00; C07H 21/04
[52] U.S. Cl. ........................... 435/6; 536/27; 935/77
[58] Field of Search ................ 536/27; 435/6; 935/77

[56] References Cited

U.S. PATENT DOCUMENTS 4,863,848 9/1989 Blöcker et al. .................. 435/6

FOREIGN PATENT DOCUMENTS 2169605 7/1986 United Kingdom .

OTHER PUBLICATIONS

Alberts et al. (1983) *Molecular Biology of the Cell*, Garland Publishing, Inc.: New York, pp. 185-187.
Szybalski (1990) *Gene*, vol. 90, pp. 177-178.
Studier (1989) Proc. Natl. Acad. Sci., vol. 86, pp. 6917-6921.

*Primary Examiner*—Ronald W. Griffin
*Assistant Examiner*—Gary L. Kunz
*Attorney, Agent, or Firm*—Kane, Dalsimer, Sullivan, Kurucz, Levy, Eisele and Richard

[57] ABSTRACT

A process for DNA sequencing by the multi-primer method involving the use of oligonucleotide banks of hexamers, heptamers, octomers, or nonamers for the creation of the primer through the ligation of two or more oligomers following hybridization onto the primer site.

3 Claims, No Drawings

PROCESS FOR DNA SEQUENCING USING OLIGONUCLEOTIDE BANK

Sequence analysis of nucleic acid fragments, especially of DNA, may be regarded as a key process in modern biological sciences and modern biotechnology. Recently, with the constant refining of sequencing techniques, the analysis even of whole complex genomes has entered the realm of the possible.

Apart from a few less popular methods, two fundamentally different methods are used particularly at the present time for sequence analysis, namely
sequencing by chemical modification and decomposition (Maxam/Gilbert method) and
sequencing by controlled polymerase addition of different nucleotides (Sanger method); cf., for example, Gassen & Schäfer, Sequenzbestimmung von Nucleinsäuren und Proteinen, in: Gassen et al, Gentechnik, 2nd edition, Gustav-Fischer-Verlag, 1987, page 241 ff.

The Sanger method can be carried out either with single-stranded DNA that is produced especially for the purpose of sequencing, or, as has been the case for some years now, with any sufficiently pure double-stranded DNA. A general characteristic of the Sanger method remains however, inter alia, the dependence of the addition enzyme (DNA polymerases) used both on a matrix (template = DNA to be sequenced) and on a starter molecule (primer). The primer is generally a short, chemically synthesised oligonucleotide that is base-complementary over its entire length with a portion positioned 3' from the DNA section to be sequenced:

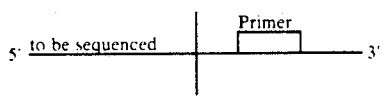

The attachment site (hybridising site) of the primer must be so selected that under the conditions of the experiment the primer finds only the desired attachment site and not any other attachment site, in order for a legible sequencing result to be obtained. The specificity of the primer depends directly on its length and on the complexity of the DNA used in the experiment. From statistical considerations and practical experience it has been found that primers having a chain length of up to 24 bases should suffice for all possible cases.

In the sequence analysis of very long DNA (for example in genome sequencing) at present essentially two different strategies are used.

Strategy 1: The Single-primer method. In this method the DNA to be sequenced is divided to a greater or lesser extent into random fragments or partially organised fragments (depending on the process variant) and then the fragments are inserted into the same vector. After cell transformation DNA preparations of individual clones are prepared and subjected to sequence analysis. Since all the DNA preparations differ at most by the inserted DNA, a single primer, which is, for example, hybridised directly adjacent to the insertion site on the vector DNA, can in principle be used for all the required sequence analyses. There are, however, considerable disadvantages weighing against this advantage:
firstly, since the clones have to be sought out randomly, individual sections of the original DNA are very often sequenced far more frequently than is necessary, and
secondly, there are often considerable yawning gaps in the collection of partial sequencing results that have been arranged in an overall sequence using suitable computer programmes, since, for example, certain sections of the original DNA to be analysed do not clone readily.

Strategy 2: The Multi-primer method. In this case the DNA to be sequenced is analysed not by the shotgun method, as in Strategy 1, but by a controlled progression. The section of the sequence to have been reliably decoded in an experiment is used to select a primer-attachment site for the next experiment and so on. The advantage of this method is especially the fact that unnecessary multiple sequence analyses like those in Strategy 1 are avoided. The essential reason why this method is not the only one used for the analysis of relatively long DNA sections probably lies in the limitation imposed by the methods of chemical DNA synthesis that are currently available.

There has been no lack of attempts to alleviate the particular disadvantages of the processes described above, for example by means of "multiplex sequencing" in Strategy 1 and the simultaneous progressive sequencing from different sites in Strategy 2. One way of eliminating altogether the essential disadvantage of Strategy 2 is, theoretically, to provide a bank of all possible primers. This is not possible in practice using direct chemical synthesis, however, since there are $4^{24}$ different primers having a chain length of 24 alone.

It is therefore proposed according to the invention that relatively short chemically synthesised oligonucleotides be used. Since any relatively long sequence may in principle be made up of two or more relatively short sequences, instead of the desired primer the short oligonucleotides corresponding to the desired primer are added to the DNA to be sequenced and by means of a suitable procedure, for example using T4-DNA ligase, are joined together to form the desired primer. The sequencing reaction can then be carried out under virtually standard conditions.

The problem on which the invention is based is solved by the subjects of the claims.

EXAMPLE 1

In typical experiments approximately 2.5 pmol DNA of the plasmid pTZ18R (Pharmacia-LKB) were denatured with NaOH, precipitated with ethanol, dried and taken up in water. 2.5 pmol of each of two different oligonucleotide solutions were added to the DNA solution. The oligonucleotides having a chain length of 8 (octamers) were so selected that they were able to hybridise immediately adjacent to each other on a section of known nucleotide sequence of the plasmid DNA. In accordance with current practice, the 5' end of the octamer that, in the hybridised state, was positioned adjacent to the 3' end of the other oligonucleotide, had previously been phosphorylated with T4-polynucleotide kinase and ATP. After the known buffer conditions for ligation with T4-DNA ligase had been established and 1 unit of the enzyme had been added, the solution (10 μl final volume) was incubated for 4 hours at 15° C. This ligation solution was stored at 37° C. for 5 minutes before the sequencing in order to allow as many 16-mers produced by ligation, and as few octamers, as possible to hybridise.

The subsequent sequencing was intended to examine the sequence of the chosen vector. For the sequencing reaction according to the standard protocol of the United States Biochemical Corporation (USB), 8 µl of the ligation solution were used. As a departure from that protocol the "annealing" of template and primer was omitted.

Where the mentioned phosphorylation had been carried out in the presence of [gamma-$^{32}$P]ATP, the later use of [α-$^{32}$P]dATP was omitted.

I claim:

1. Process for DNA sequencing by the multi-primer method which comprises:
    (a) selecting in the DNA to be sequenced a single-stranded primer-attachment site of known sequence;
    (b) hybridizing immediately adjacent to each other at the primer-attachment site two oligonucleotides selected from the group consisting of hexameric, heptameric, octameric and nonameric oligonucleotides obtained from a bank comprising all possible $4^6$, $4^7$, $4^8$ an d$4^9$ different oligonucleotides;
    (c) hybridizing simultaneously with step (b) or after step (b) a further hexameric, heptameric, octameric or nonameric oligonucleotide immediately adjacent to one of the other two oligonucleotides at the primer-attachment site,
    (d) ligating the oligonucleotides to form a primer, and
    (e) heat treating to remove non-ligated oligonucleotides.

2. Process according to claim 1, characterized in that at the primer-attachment site two oligonucleotides are hybridized and ligated with one another to form a pre-primer and only then is a third oligomer hybridized and ligated to the pre-primer at the primer-attachment site.

3. Process according to claim 1, characterized in that there are used oligonucleotides that are phosphorylated at their 5' end when that end is to be ligated with an adjacent oligonucleotide with the aid of T4-DNA ligase.

* * * * *